(12) United States Patent
Brophy et al.

(10) Patent No.: US 7,118,920 B2
(45) Date of Patent: Oct. 10, 2006

(54) MULTIPHASIC MICROCHANNEL REACTIONS

(75) Inventors: John H. Brophy, Bristol (GB); Bruce F. Monzyk, Delaware, OH (US)

(73) Assignee: Battelle Memorial Institute, Columbus, OH (US)

( * ) Notice: Subject to any disclaimer, the term of this patent is extended or adjusted under 35 U.S.C. 154(b) by 473 days.

(21) Appl. No.: 10/279,090

(22) Filed: Oct. 22, 2002

(65) Prior Publication Data

US 2004/0082804 A1 Apr. 29, 2004

(51) Int. Cl.
 *B01J 8/02* (2006.01)
 *C07C 239/00* (2006.01)
 *C07C 241/00* (2006.01)
 *C07C 255/00* (2006.01)

(52) U.S. Cl. ............... 436/183; 436/180; 436/181; 502/164; 564/301; 564/305; 558/451; 568/471; 422/211; 422/130

(58) Field of Classification Search ......... 422/211, 422/130, 101; 560/1, 60; 436/180, 181, 436/183; 570/260; 502/164; 564/301, 305; 558/451; 568/471
See application file for complete search history.

(56) References Cited

U.S. PATENT DOCUMENTS

| | | | | |
|---|---|---|---|---|
| 4,754,089 A | | 6/1988 | Matson et al. ............... 570/260 |
| 6,225,497 B1 | * | 5/2001 | Becker et al. ............... 560/347 |
| 6,488,838 B1 | * | 12/2002 | Tonkovich et al. ......... 208/108 |
| 6,515,189 B1 | | 2/2003 | Harston ....................... 568/939 |
| 6,749,814 B1 | * | 6/2004 | Bergh et al. ................. 422/130 |
| 6,890,493 B1 | * | 5/2005 | Bergh et al. ................. 422/130 |
| 2002/0106311 A1 | | 8/2002 | Golbig et al. |
| 2005/0009175 A1 | * | 1/2005 | Bergh et al. .............. 435/287.2 |
| 2005/0087767 A1 | * | 4/2005 | Fitzgerald et al. .......... 257/200 |
| 2005/0154226 A1 | * | 7/2005 | Liu et al. ..................... 560/240 |

FOREIGN PATENT DOCUMENTS

| | | |
|---|---|---|
| DE | 10063027 A1 | 6/2002 |
| WO | WO 96/12540 | 5/1996 |
| WO | WO 97/00442 | 1/1997 |
| WO | WO 03/103836 A1 | 12/2003 |
| WO | WO 2004/050799 * | 6/2004 |

OTHER PUBLICATIONS

PCT International Search Report, PCT/US03/33105, mailed Apr. 22, 2005.
Hisamoto et al., "Fast and high conversion phase-transfer synthesis exploiting the liquid—liquid interface formed in a microchannel chip," Chem. Commun. 2662-2663 (2001).

* cited by examiner

*Primary Examiner*—N. Bhat
(74) *Attorney, Agent, or Firm*—Barry Bissell; Frank Rosenberg (57) ABSTRACT

Multiphasic reactions, especially those reactions using a phase transfer catalyst, are conducted in microchannel apparatus. Advantageously, these reactions can be conducted with two, planar microlayers of reactants in adjacent laminar flow streams. Microchannel apparatus and methods for conducting unit operations such as reactions and separations in microchannel apparatus is also described. Microchannel apparatus can provide advantages for controlling reactions and separating products, solvents or reactants in multiphase reactions.

18 Claims, 6 Drawing Sheets

MULTIPHASIC MICROCHANNEL REACTIONS

FIELD OF THE INVENTION

The present invention relates to multiphasic reactions conducted in microchannels, and apparatus for conducting such reactions.

BACKGROUND OF THE INVENTION

Many chemical reactions are conducted without solvents or in a single solvent phase. Other chemical reactions are conducted in multiple solvents, normally two, that are not miscible with each other, or at least have low mutual solubilities,—these processes are called multiphasic reactions. Some of these multiphasic reactions provide advantages such as: enabling the reacting of dissimilar polarity reactants, (for example non-polar materials reacting with polar materials, ions with neutral compounds, ions with compound having no net dipole, etc.), faster reaction rates, higher selectivity, better yield, fewer undesired side products, less chemical waste, lower process temperatures, greater safety, easier separation of products, lower energy use, lower raw material costs, avoidance of solid products, or a more environmentally-friendly process.

Along with the potential benefits, there are many potential difficulties with multiphasic processes. For multiphasic reactions in which one reactant is in one phase and a second reactant is in a second phase, the rate of reaction can be very slow due to slow interphase transport, or due to very low solubility of one or more reactants in the second phase, where the main reaction occurs. A phase transfer catalyst (sometimes abreviated as "PTC") can be used to increase the rate of a reactant (or reactants) moving between phases and/or the apparent solubility of one or more of these reagents in the other phase, and thus increase the rate of a multiphasic reaction (chemical reaction rates are normally proportional to the activity of the reactants in the same phase). Examples of PTCs include organoammonium compounds (RR'R"R'"$N^+X^-$), carboxylic acids (RR'COOH) and their salts and complexes with metal ions ($M^+$), organophosphonium compounds (RR'R"$P^+R'"X^-$), mono, di and poly alcohols (RR'R"COH), mono, di and poly ketones (RCOR'), phosphoric acid, (O=P(O—R)(O—R')(O—H) (mono and diesters), and phosphate esters (O=P(O—R)(O—R')(O—R), phosphorus acid esters (O=P(R)(O—R')(O—H), and phosphonate esters (O=P(R)(O—R')(O—R), phosphinic acid esters (O=P(R)(R')(O—H), and phosphinate esters ((O=P(R)(R')(O—R"), and ethers (ROR'), where $X^-$ is any anion, and $M^+$ is any metal ion. RR'R"R'" can be the same or different consisting of H or any alkyl and/or aryl group as pure hydrocarbons (with CN>4), mixtures of hydrocarbons (with CN>4), alone and/or also containing substituents such as $Cl^-$, $Br^-$, I, $NO_2^-$, —$OH^-$, OR, —COOR, and mixtures thereof, where R""=any alkyl and/or aryl group as pure hydrocarbons, mixtures of hydrocarbons, and/or also containing substituents such as $Cl^-$, $Br^-$, $I^-$, $NO_2^-$, —$OH^-$, OR, —COOR, —CN, —NRR', alkyl, aryl, and the like, and mixtures thereof. In the above lists all "R" groups are organic with CN>4 for the total molecule, or at least 1 for any given substituent. R can be H if the rest of the molecule has a CN of at least 4. It is only necessary that the entire molecule has at least some ($>10^{-8}$M) solubility in at least two of the liquid phases present.

Over the years, many attempts have been made to improve multiphasic reactions. Substantial efforts have been made to use apparatus with small internal dimensions to increase the rate of biphasic reactions. For example, Matson et al., in U.S. Pat. No. 4,754,089 (issued in 1988), described phase transfer catalysis in a multiphase reaction system in which the different phases are separated by a membrane permeable to the phase transfer catalyst. An example was described in which a hydrophobic membrane was sandwiched in between flow channels that were 0.05 cm deep, 10 cm wide, and 20 cm long. This patent includes descriptions of phase transfer catalysts and catalyzed reactions that are incoporated by reference herein.

Schubert et al., in Canadian Patent No. 2,236,460A1, describe the use of a microchannel mixer for forming fine dispersions for chemical reactions. Similar apparatus is described in U.S. Pat. Nos. 6,225,497 and 6,264,900.

Nakajima et al., in U.S. Pat. Nos. 6,155,710 and 6,258,858 reported forcing a dispersed phase through a narrow gap to form an emulsion with the dispersed phase in droplets of a predetermined diameter. In the later patent, the inventors suggest that microchannels can be used to separate some of a continuous phase from a dispersed phase.

Despite these and many other efforts, such technologies suffer from slow kinetics due to long internal diffusion paths, difficulty in obtaining quick phase separation, variable performance due to lack of control over internal fluid dynamics and interchannel mixing of contents, unstable phase interfaces under flow shear, volume expansion and associated phase—phase displacement due to absorption of one phase of small portions of the other phase, and others. Hence there remains a need for novel methods and apparatus for conducting multiphasic reactions.

SUMMARY OF THE INVENTION

Confinement of thin immiscible streams and exploiting control over laminar flow in microchannels provides a large contact surface area between immiscible phases for improved reactivity and/or fluid separation, and avoids the normal requirement for mechanically mixing of the two phases. Additionally or alternatively, a means is provided for the quick inducement of phase separation of the product reaction mixture.

In one aspect, the invention provides a method of conducting a chemical reaction, comprising: providing a first stream having a thickness of 1 mm or less and a length of more than 3 mm; and providing a second stream adjacent the first stream and having a thickness of 1 mm or less and a length of more than 3 mm; wherein the first stream and the second stream form a combined multiphase stream having a thickness of 2 mm or less and a length of more than 3 mm. The first stream comprises a first reactant and the second stream comprises a second reactant. A phase transfer catalyst catalyzes the reaction of the first reactant and the second reactant to form a product. In cases where thickness of a phase varies, the "thickness" referes to the maximum thickness in a microchannel reaction zone (i.e., in a microchannel where PTC occurs).

In another aspect, the invention provides a phase transfer catalysis system, comprising: a first stream having a thickness of 1 mm or less and a length of more than 3 mm disposed in a reaction channel having a thickness of 2 mm or less and a length of more than 3 mm. In this system, a second stream is adjacent to the first stream and has a thickness of 1 mm or less and a length of more than 3 mm in the reaction channel. The first stream and the second stream form a combined multiphase stream having a thickness of 2 mm or less and a length of more than 3 mm. The first stream comprises a first reactant and the second stream comprises a second reactant. A phase transfer catalyst catalyzes the reaction of the first reactant and the second reactant to form a product (by "a product" it is meant at least one product).

In another aspect, the invention provides microchannel apparatus, comprising: a first channel inlet connected to a reaction channel having a thickness of 2 mm or less and a length of more than 3 mm; wherein the reaction channel comprises a ceiling and a floor and wherein the floor and the ceiling each define a border of an open area and wherein the thickness of the reaction channel is the distance between the ceiling and the floor. A second channel inlet is connected to the reaction channel. A separator plate separates the first channel inlet from the second channel inlet; wherein an edge of the separator plate forms at least one border of the open area; and wherein the open area has a length of at least 3 mm. There is no membrane in the open area. A first channel outlet is connected to the reaction channel; and a second channel outlet is connected to the reaction channel. The second channel outlet is separate from the first channel outlet.

The invention also provides a method of making microchannel apparatus comprising: stacking a first sheet, a second sheet, a third sheet, a fourth sheet and a fifth sheet in the order such that the first sheet overlies the second sheet which overlies the third sheet which overlies the fourth sheet which overlies the fifth sheet; and bonding together the first, second, third, fourth and fifth sheets. The sheets have designs such that, in the bonded device the first sheet forms a ceiling for an open area, the fifth sheet forms a floor for the open area, the second sheet comprises a first stream inlet connected to an open channel and a first stream outlet connected to the open channel, the fourth comprises a second stream inlet connected to the open channel and a second stream outlet connected to the open channel, and the third sheet comprises a separator plate that separates the first stream inlet from the second stream inlet. "Bonding" refers to any process of holding the sheets together.

In yet another aspect, the invention provides microchannel apparatus, comprising: a separation zone that comprises: at least one portion of an internal surface that is hydrophilic; at least one portion of an internal surface that is hydrophobic; and at least one separation assist feature selected from the group consisting of: an expansion zone in the separation zone that is connected to a reaction channel and has a larger internal cross-sectional area than the reaction channel, a phase coalescence agent, and a separator plate. The separation zone has at least one internal dimension of 2 mm or less.

In a further aspect, the invention provides a method of conducting at least one unit operation, comprising: passing a multiphasic fluid stream into a separation zone; wherein the multiphasic steam comprises a first non-solid phase and a second non-solid phase; wherein the separation zone comprises: at least one portion of an internal surface that is hydrophilic; at least one portion of an internal surface that is hydrophobic; and at least one separation assist feature selected from the group consisting of: an expansion zone in the separation zone that is connected to a reaction channel and has a larger internal cross-sectional area than the reaction channel, a phase coalescence agent, and a separator plate. The multiphasic fluid stream passed into the separator zone has at least one dimension of 2 mm or less. At least two separate streams pass from the separator zone; these streams are called a first separated stream and a second separated stream. The first separated stream contains a relatively higher ratio of the first non-solid phase to the second non-solid phase as compared to the multiphasic fluid stream entering the separator zone; and the second separated stream contains a relatively lower ratio of the first non-solid phase to the second non-solid phase as compared to the multiphasic fluid stream entering the separator zone.

In another aspect, the invention provides apparatus and methods for separating phases from a microchannel. This could be accomplished by a stream splitter, preferably a plate with one major surface selected to attract a first phase and the other major surface selected to attract the second phase. Preferably, a two phase "layered" stream is split by the plate into separate phases. In a particularly preferred embodiment, the plate has a sharp blade tip (with the two layered stream flowing into the tip) expanding into a thicker plate body or wedge shape. Two phases provided in that the "roof" and "floor" of the separator region of the channel, or separator channel, have opposite surface polarities and/or wettabilities. For example, for oil/water mixtures, in which the oil phase is less dense than the aqueous phase, the "roof" of the channel has a hydrophobic surface and the "floor" a hydrophilic surface.

The invention also includes use of the apparatus described herein for phase transfer catalysis and apparatus during operation. For example, in some aspects, the invention can be described as apparatus containing two immiscible phases as described herein. The invention should also be understood to include individual reactions, individual classes of reactions and selected reaction types.

Uses for the invention include the production of bulk, speciality, and fine chemicals, and for pollution prevention, for example, to remove or destroy impurities in waste or product streams. The invention is not limited to these uses, but extends to the full range of applications for multiphasic reactions.

Advantages of various embodiments of the invention may include one or more of the following: smaller reactor size, decreased number of unit operations, lower costs, simplified apparatus and method steps, increased reaction rate, improved yields, increased selectivity, fewer undesired side products, lower energy requirements, excellent control of temperature and residence time, lower inventories of materials, especially highly reactive and/or toxic matreials, lower cost raw materials, more choice of materials for reactors, including plastic, ability to use smaller reactors with the same or greater productivity as larger volume reactors, processes that have a lower fouling tendency, plug flow concentration profile instead of continuously stirred tank reactor (CSTR) (normal for continuous industrial manufacturing of chemicals and for separations), and greater safety, less risk in handling toxic or reactive intermediates.

The subject matter of the present invention is particularly pointed out and distinctly claimed in the concluding portion of this specification. However, both the organization and method of operation, together with further advantages and objects thereof, may best be understood by reference to the following description.

GLOSSARY OF TERMS USED

"Adjacent" means directly in contact without a membrane separating the streams.

"multiphase" means at least two non-solid phases.

"Reaction channel" refers to a channel in which, during operation, there are at least two continuous phases and a PTC.

"Hydrophobic" and "hydrophilic" materials are generally known in the art; however, for closely related wettability materials, resort may be had to measurement of advancing contact angle in an automated goniometer where hydrophobic materials have an advancing contact angle of at least 90 degrees for distilled water and hydrophilic materials have an advancing contact angle of 90 degrees or less. A suitable test for measuring contact angle is ASTM D5725-99. It is important to note that, in the present invention, hydrophilicity and hydrophobicity are intrinsic properties of a material and are to be defined with reference to a sheet or flat article and not a microchannel in order to avoid capillary effects that would influence contact angle.

A phase transfer catalyst (PTC), facilitates the bringing together of either:

1) a chemical reaction catalyst (CRC, or just "C") and a reagent (e.g. species "A") into contact with each other (i.e. A+C→P+C, where P=product), or 2) C brings A together with at least one more reactant (e.g. B), present in a second fluid immiscible with the first, so that the two reagents can react (i.e. A+B+C→P+C).

"Facilitates" means that the PTC can bond to (ionically, covalently, or coordinate covalently) the catalyst or reagent, e.g. PTC+C→C–PTC, or allow C to transfer across the liquid-liquid interface indirectly by bonding to the chemically unreactive ("inert") counter ion of the reactive species (A or B).

Typically, for soluble PTCs, the effectiveness of a PTC can be achieved at low levels in the opposite phase (e.g., $1 \times 10^{-6}$ to 0.01 M). Higher concentrations are functional but not normally needed and only serve to waste the PTC. The distribution coefficient for the PTC can be low, but preferably not so low as to not speed up the rate of the reaction of interest. The PTC is typically thought to exist in bulk solution of both phases, but not normally at the same concentration, and so is not restricted to interfacial activity and surface area. The PTC is used numerous times per contact, for example, thousands to millions of times per contact.

In most embodiments, the PTC will be soluble in at least one phase (and typically two phases); however, in some embodiments, the invention may employ a three phase system with an insoluble PTC either as a third liquid phase or a solid phase such as an immobilized phase transfer catalyst on a particle support.

On the other hand, extractants (E) are typically used at much higher levels, normally 2–25%, (or even neat, i.e. essentially 100%), in a diluent solvent, often with a solubility modifier, where they bond to at least one solute in a first phase (thought to occur at the interface between the two liquids), making that solute now soluble in the second phase into which it can now partition. The solute is not reacted in the second phase in the microchannel but is typically transported out and separated from the extractant in a second similar, but opposite, reaction. The extractant is used just once per contact. The distribution coefficient for the extractant, modifier and diluent should all be selected to be as high as possible, >1 and often 1000–10,000.

BRIEF DESCRIPTION OF THE FIGURES

FIG. 6b is a schematic illustration of the circled area in FIG. 6a.

DESCRIPTION OF PREFERRED EMBODIMENTS

Phase Transfer Catalysis

A phase transfer catalyst shuttles reactive species across the phase boundary between immiscible phases. In a typical example, a quaternary ammonium salt ("quat") is added to an aqueous phase where it forms an ion pair with a dissolved reactant, for example hydroxide ion ($OH^-$). For example the aqueous phase may contain sodium hydroxide reactant and the quat salt is the readily available chloride salt, i.e., (1)

where the comma designates an ion pair within either phase, in this case the aqueous phase (aq). The ion pair, $RR'R''R'''N^+,OH^-_{(aq)}$, which is soluble in the organic phase, transfers ("partitions") according the the thermodynamic (equilibrium) partition coefficient for this ion, $P_{R4NOH}$, the dissolved reactant into the organic phase to form $RR'R''R'''N^+,OH^-_{(org)}$, i.e., (2)

where it catalyzes a reaction with a reagent dissolved in the organic phase, for example the saponification (hydrolysis) of an oil soluble methyl ester $R_1COOCH_3$, (e.g. where $R_1CN$ is >5), as follows,

(3)

followed by, (4)

Hence the $RR'R''R'''N^+,OH^-_{(org)}$ species is regenerated, illustrating its catalytic nature. Depending on the CN of the product alcohol and acid they separately may or may not distribute into the aqueous phase.

Therefore, following the reaction, the phase transfer catalyst is released and partitions back into the aqueous layer to repeat the cycle, hence accelerating the rate in which the two reactants encounter each other, and hence the PTC enhances the overall reaction rate, i.e., (5)

where $k_{cat} \gg k_{ucat}$ and parenthesis indicate solute activities. Enhancements of many orders of magnitude are routine, making PTC a powerful and frequently used tool of chemical manufacturing.

Preferred phase transfer catalysts have hydrophobic and hydrophilic moieties in the same molecule, are soluble in aqueous solutions and yet have high oil/water partition coefficients, and preferably not foam-forming or emulsifier surface active agents as are the related types of molecules known as surfactants, detergents, or soaps, or emulsifiers (for example butoxy ethanol such as are the Cellosolve®s). Although not preferred, these reagents are functional as PTCs and as such are included in this invention. PTCs known in the prior art for bulk chemical processing are suitable for use in the present invention[1].

For reagents and catalysis involving water soluble anionic reactants, such as permanganate, perchlorate, chromate/dichromate, halide (F, Cl, Br, I), cyanide, thiocyanate, tri-iodide, molybdate, tungstate, polyoxometallates, hydroxide, formate, acetate, propionate, benzoate, sulfonates, sulfates, bicarbonate/carbonate, other pseudo halides, and the like, the PTC is preferably a quaternary ammonium ion, more preferably a tetraorganoammonium compound, preferably having a total carbon number of 4 or greater. Examples of perferred quats are available from SACHEM, Inc. (http://chem.com/Sachem/catalog.html). The organo group can be a straight chain alkyl (such as four n-butyl, or one n-octyl to n-tetradecyl and the other three methyl), but could be branched chain, and/or include aromatic groups, such as phenyl and benzyl groups. The C1 to C4 R groups (4–16 total carbons, including both straight and branched chain) of the above Sachem reference are also effective. Additional groups may also be present in the PTC molecule, such as halogens, nitro groups, pseudo halogens, etc. provided that the final compound possesses a positive net molecular charge, positive in the case of quats, and so long as the oil/water partition coefficient is still large enough to affect the desired reaction rate enhancements via catalysis of solubility. Examples of tetraorganoammonium PTCs include $Br^-$, I, $CH_3COO^-$, phthalate, perchlorate, chromate, permanganate, fluoride, nitrate, hydrogen sulfate, methanesulfonate, nitrite, fluoroborate, fluorophosphate, trifluoroacetate, or $Cl^-$ salts of the cations: $^\oplus NEt_3(C_4H_9)$, $^\oplus N(C_4H_9)_3 Et$, $^\oplus N(C_4H_9)_3 Me$, $(C_6H_5CH_2)N^\oplus Et_3$, $(C_6H_5CH_2)N^\oplus Me_3$, $(C_4H_9)_4 N^\oplus$, $^\oplus N(C_8H_{17})_3 Me$, and $(C_{16}H_{33})N^\oplus Me_3$. Other suitable PTCs for anionic reactants include: quaternary arsonium salts (such as $AsPh_4^+$), quaternary phosphonium salts, preferably tetraorganophosphonium salts such as $^\oplus P(Ph)_4$, $^\oplus P(Ph)_3 R$ (where R is an alkyl such as methyl, ethyl, propyl or butyl), $^\oplus P(C_4H_9)_4$, and organo carboxylics (e.g. organo cobaltic complexes, for example Co(naphthenate)$_2$). Less preferred anion pairing PTCs include lignosulfonates, and sulfate, dibasic phosphate, due to their low partition coefficient. Co-catalysts may be present and can include species such as alcohols (preferably diols) and tungstate ions. PTCs are known in the art and various reviews are available, such as, "Phase Transfer Catalysis: Fundamentals, Applications, and Industrial Perspectives", by C. M. Starks, C. L. Liotta, and M. Halpern, Chapman & Hall, 1994.

For catalysis involving cationic reactants, such as Cu, Mn, Fe, Ag, Ce, Co, Ti, Zr, etc., oil soluble, monodentate complexing and chelating complexing ligands are preferred. These PTC's displace all or part of the water around the cation to impart the needed hydrophobicity and charge neutralization to make the cation oil soluble (preferred partition coefficient >1) and yet still retain the metal ion in a reactive form. Examples of such complexing and chelating compounds with a total carbon number of 8 or more, can be selected from carboxylic acids, organophosphates, organophosphonates, organophosphinics, organophosphine oxides, heterocyclic amines, organoamines (including polyamines), organo amide oximes, keto-oximes, crown ethers, alkyl phenols, and diketones (such as organoacetylacetonate).

Neutral complexing molecules such as polyethylene glycol, cryptands, crown ethers (for example, dicyclohexano-18-crown-6, dibenzo-18-crown-6, 18-crown-6, and 15-crown-6) and cyclodextrins can also be used as PTCs and are preferred PTC's in some embodiments.

For PTC-promoted catalysis involving neutral but water soluble reactants, such as hydrogen peroxide, acids, and hydrogen gas—a reagent can be shuttled into the organic phase by forming an organic soluble adduct, by solvation, or by intermediate compound formation. In the case of hydrogen peroxide, an insertion intermediate is formed using an oil soluble raw material sufficient to form hydroperoxides. For example, organo-boronic acids can be used as PTCs to form hydroperoxides that partition into nonpolar cyclohexane producing a blend of cyclohexanol and cyclohexanone. Ti(III), Mn, Fe(II) and Co(II) complexes can carry the peroxide moiety.

Hydrogen gas/oil represents a gas/liquid two phase system under this invention. For hydrogen, organometallic complexes that form oil soluble hydrides with $H_2$ adduct can be used. Such organometallic complexes can be prepared from complexes of Co, Fe, Mn, Mo, Pd, Ni, Ti, and the like.

Ethers and ketones can be used to transfer acids, such as HCl, or neutral metal salts, such as aluminum chloride or iron(III) chloride, zinc chloride, copper(I or II) chloride, and their salts with iodide or bromides used alone or in any combination.

In some embodiments, aqueous-aqueous (Aq—Aq) and Double Emulsion Liquid-Liquid Extraction (DE-LLX) systems may be used in this invention as the respective fluids behave in the same fashion as normal Liquid-Liquid Extraction (LLX), and have the advantage that they allow protein-based, i.e. enzymatic, catalysts to be used in LLX systems, which otherwise normally use non-aqueous fluids to achieve water immiscibility and these solvents denature (degrade) proteins, including enzyme catalysts.

In most embodiments, the PTC will be soluble in at least one phase (and typically two phases); however, in some embodiments, the invention may employ a three phase system with an insoluble PTC either as a third liquid phase or an immobilized phase transfer catalyst on a particle support. Depending depending on the reaction, the insoluble PTC approach can provide some improved reaction conditions. For example, the chloride-bromide exchange of benzyl chloride with sodium chloride using tetrabutylammonium salts as the PTC. This system forms a three phase reactive system: organic phase (toluene), PTC phase, and aqueous phase. The rate of reaction for this reaction increases significantly once enough of the PTC is added to form the third PTC phase. Theoretically, both organic and inorganic reagents are transferred to this third phase where the intrinsic reaction takes place. The formation of the third phase can also occur in oil-water emulsion systems where the PTC phase can contact the organic phase.

Apparatus

Figure 1:
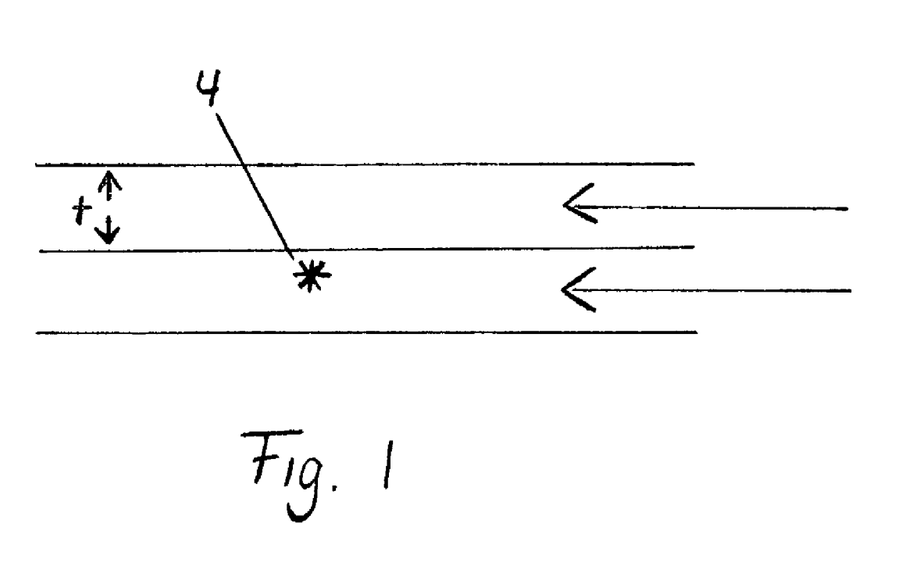
FIG. 1 schematically illustrates adjacent streams with a phase transfer catalyst.

Schematic illustrations of apparatus with two phases are shown in the Figures. FIG. 1 illustrates a cross-sectional view of a reaction configuration in which two immiscible phases, phase 1 and phase 2, flow adjacent each other. The thickness of at least one of the phases is controlled to have a thickness, t, of 1000 micron (μm) or less, preferably <100 μm, and most preferrably <10 μm. A PTC 4 is present in at least one of the streams. In some preferred embodiments, the stream has a thickness of 100 μm or less, and in some embodiments, in the range of 0.1 μm to 10 μm. Thickness is measured perpendicular to flow. In some preferred embodiments, both streams are controlled to have thicknesses in these ranges. Preferably, one or both phase streams have an area to volume ratio of at least 10 cm$^{-1}$, more preferably at least 100 cm$^{-1}$. For example, a stream with dimensions of 4 cm×4 cm×0.01 cm has an area to volume ratio of 100 cm$^{-1}$. In the typical mode of operation, for obvious reasons, the less dense stream is on top relative to the gravitational field. A phase density difference of at least 0.05 g/cc is preferred, though systems with less of a difference are effective.

FIGS. 2A–E illustrate top down views of thin plates that could be stacked and bonded to form a microreactor for phase transfer catalysis. A cover plate A contains first phase inlets 12 and first phase outlets 22. The thin plates are also known as "shims." Shim B has first phase passages 14 and 16. During operation of the assembled device, the first phase enters shim B through passage/plate inlet 14, traverses the plate through planar reaction zone 15 (which is simply an opening in Shim B), and exits through first phase passage/plate outlets 16. Border material 17 prevents the second phase from flowing out of second phase passages 18. Optional shim C may provide a border material 21 that, in the assembled device, helps prevent phase mixing (and formation of a discontinuous phase) near the plate inlets. Shim D is analogous to shim B except that, in the assembled device, it provides for flow of the second phase stream through planar reaction zone 23. Cover plate 25 shown in FIG. 2E contains second phase inlets 13 and second phase outlets 26.

It should be appreciated that numerous variations of the configuration are possible. For example, the device could alternatively be plumbed so that the first phase inlet and the first phase outlet are on opposite sides rather than the same side of the device as illustrated in the figures. It should also be understood that the shims, for example shims B and D (and, optionally, shim C) can be repeated any number of desired times to form multiple, parallel reaction zones within a single device.

FIG. 2F illustrates a cross-sectional view of the device formed by stacking and bonding shims A–E. Arrows drawn in streams 31 and 33 illustrate flow of the first and second phases through the devices. During operation, a PTC shuttles a reactant between flow streams, thus increasing the rate of reacting a reactant in the first phase stream 31 with a reactant in the second phase stream 33. A product in a flow stream can be separated or passed into another device or another section of an integrated device. In some preferred embodiments, some or all of an exiting phase stream is recycled into an inlet of the same device or another reactor. In the present invention, optional shim C provides an open area and not a membrane. Membranes are undesirable because of the added cost, added complexity, and because they form a barrier to rapid exchange of reactants between streams.

Also shown in FIG. 2F are separator plates 21 having surfaces 32, 34 that can be modified to have differing degrees of hydrophilicity to assist in attracting a desired phase and repelling an undesired phase for better stream separation. The separator plates have edges that define one border of open area 34. Also shown are first phase channel inlet 31 and second phase channel inlet 33. Endplates A and E form reaction channel ceiling 9 and reaction channel floor 25.

In some preferred embodiments of the present invention, flow streams are continuous—in other words, the flow streams are continuously moving in the reaction zone. In some preferred embodiments, the adjacent phases are planar and in contact for a length (measured in the direction of flow) of at least 1 mm, and in some embodiments 10 to 1000 mm. A system is known to exist in Laminar flow depending on its density, viscosity nd flow rate according to the equation for Reynolds' numbers ($N_{Re}$, where $N_{Re}=DV\rho/\mu$). Calculations using this equation provide the means to determine whether a particular design demensions, flow rate and fluid viscosity will yield laminar or tubulent flow. A Reynolds' number of 1800 or less is essentially completely laminar and is most preferred. This equation will allow the user to ensure the design is in the laminar flow regime. Also, it is well known in the art that turbulence takes some distance to develop in a flowing fluid, extending in Reynold's numbers from >1800 to about 25,000. Hence many of these flow rate conditions can be accomodated by the invention by using shorter contact distances with increasing Reynold's numbers in the range of 1800 to 25,000. Above 25,000 turbulence is complete and therefore is least prefered for the non-emulsifying aspect of this invention. This $N_{Re}$ calculation defines the range of flow velocities for laminar flow in devices of the invention. Note that these calculations involve the dimensions of the microchannels used, and hence predicts target design dimensions of the internal channels of the device.

In some preferred embodiments, interphase mixing and/or emulsion breakage into the respective immiscible phases, are promoted by constructing the MTP device to have at least two internal surfaces having differing degrees of hydrophobicity selected to attract or repel the desired phases. For example, separator 21 can have a hydrophilic surface (such as a silica, hydrophilic silicone, hydrophilic silane, alumina, plastic rendered hydrophilic by virtue of a surface treatment with alcohols, amines, high energy treatment (for example, electron beam or plasma) and other nonpolar plastics such as polymethacrylates, etc.) 32, and a hydrophobic surface 34 (such as hydrophobic silicone, hydrophobic silane, perfluorination, hydrophobic plastic (e.g. polyolefins, polystyrene, ABS, SAN, polysulfone, etc.), so that the fluid emulsion droplets and continuous phase, and their product coalesced fluids can wet and adhere to the appropriate surface of like polarity, and thereby resist beading and forming, or re-forming, droplets and/or a dispersed emulsion. In some preferred embodiments, the separator is very thin to avoid turbulence and mixing. Preferably, the separator has a thickness (t) set to laminar flow using the $N_{Re}$ values as described above.

Figure 3:
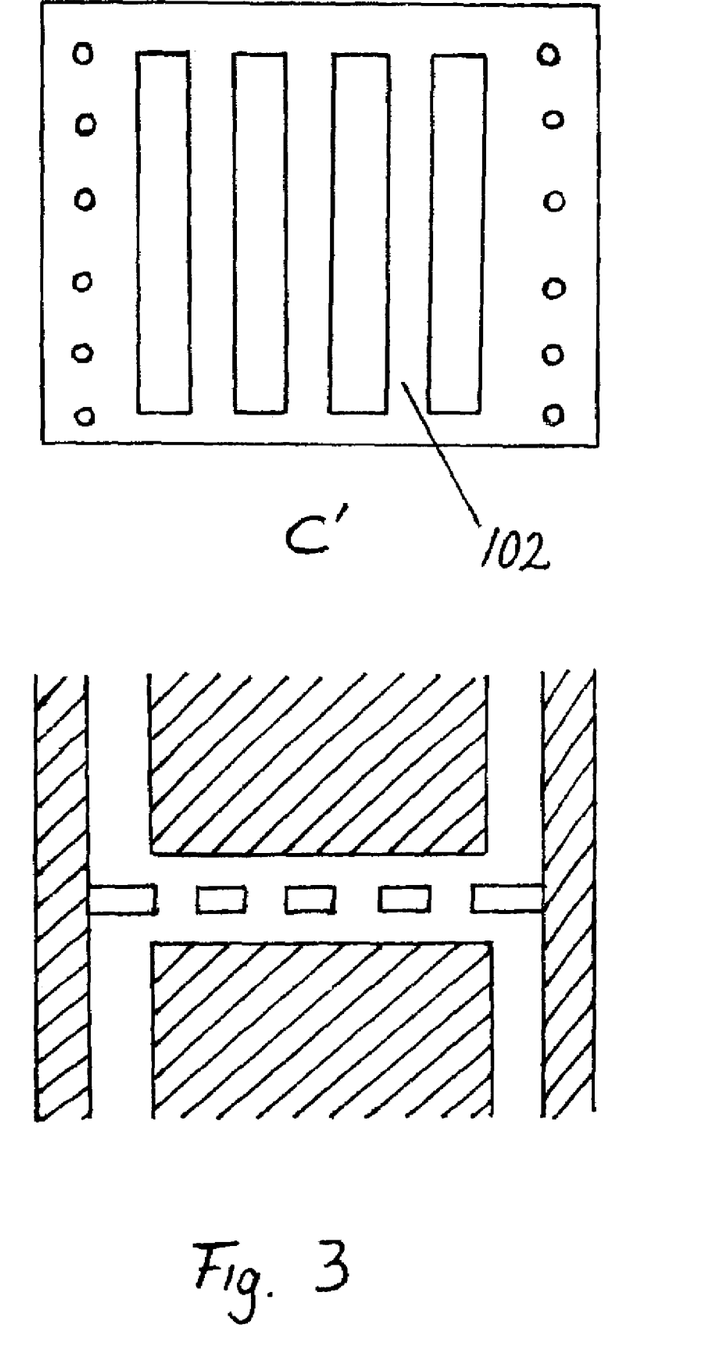
FIG. 3 illustrates a plan view of an alternative sheet design (C') and a schematic, cross-sectional view of a device utilizing the alternative design.

FIG. 3 (top) shows an alternate design for optional shim C' with ribs 102 that help prevent formation of a dispersed phase. FIG. 3 (bottom) shows a cross-sectional view of the assembled device.

Figure 2:
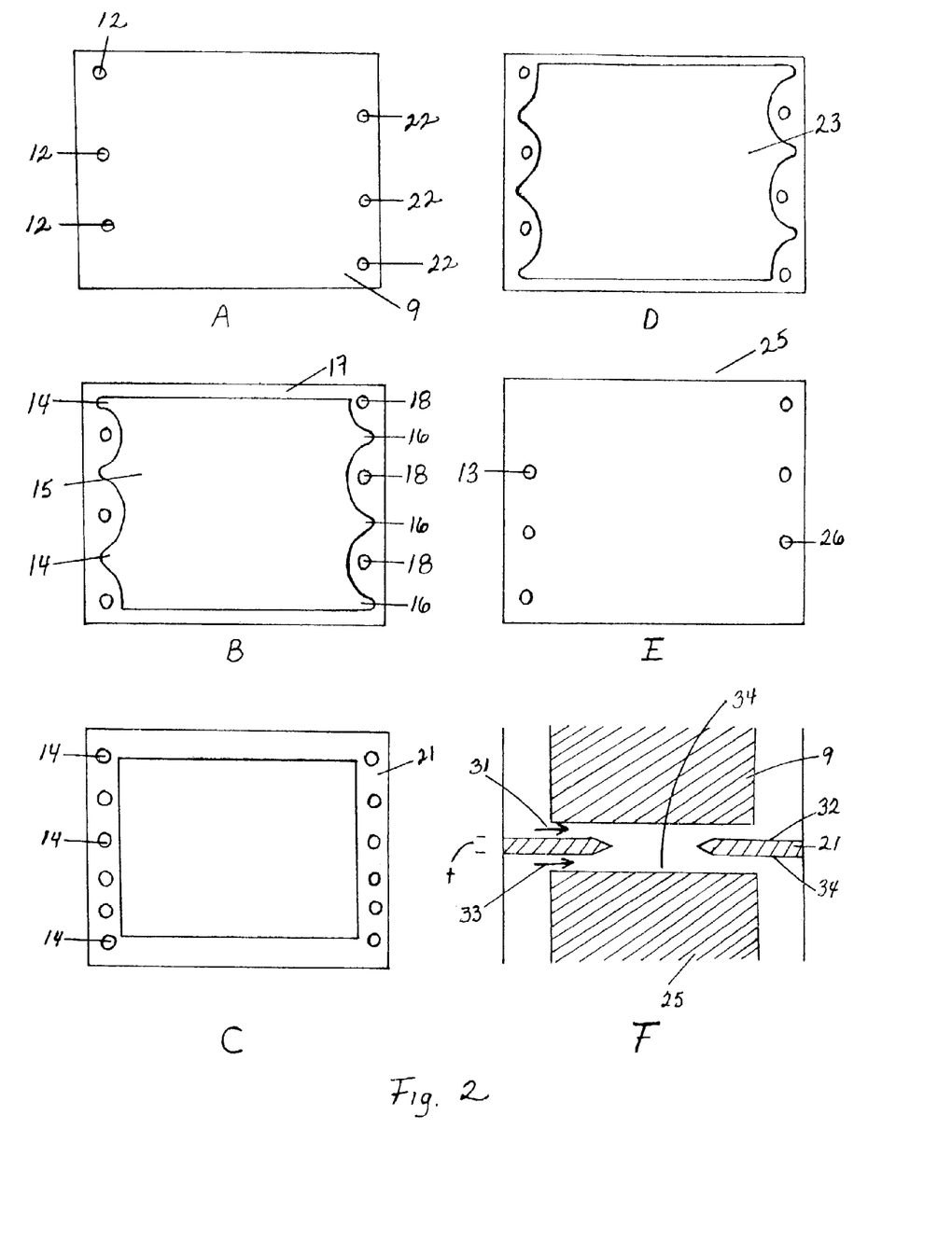
FIGS. 2A–2E show plan views of sheets that can be stacked and bonded to form a laminated device for phase transfer catalysis.
FIG. 2F is a schematic, cross-sectional view of a device formed by laminating the sheets of FIGS. 2A–2E.
Figure 4:
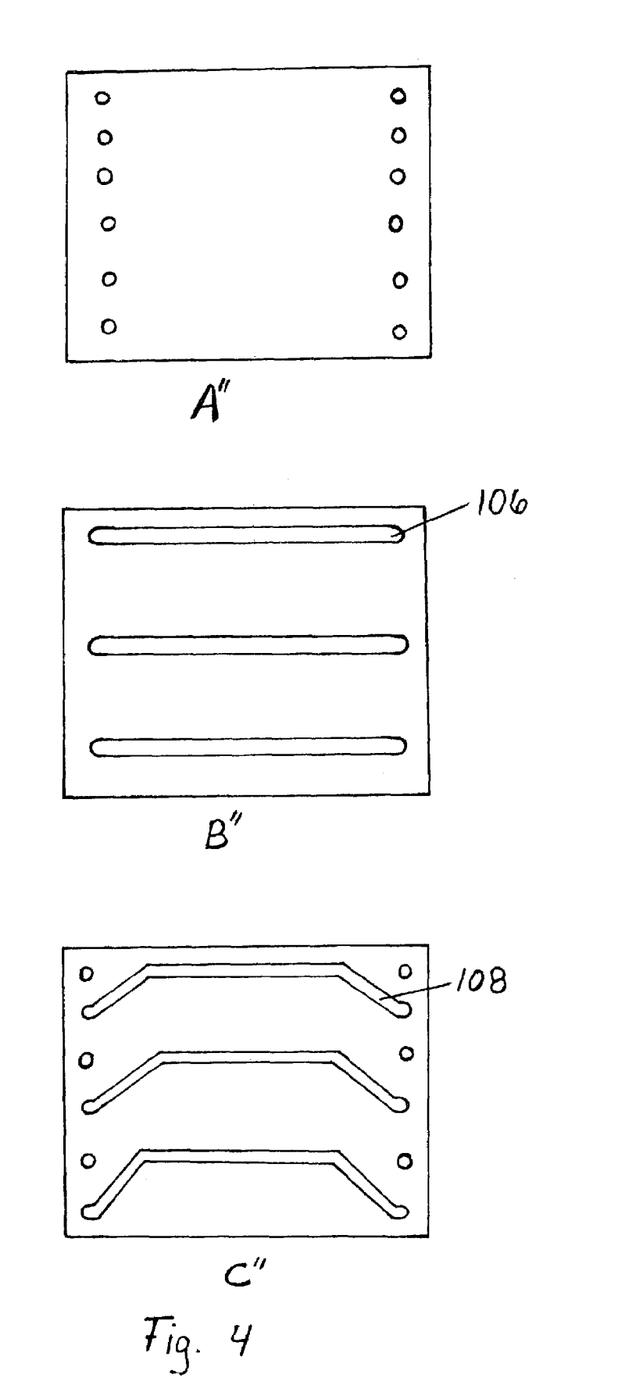
FIG. 4 illustrates plan views of sheets that can be included in a laminated device for phase transfer catalysis in channels. In some embodiments, these sheets (A", B", and C") are substituted in place of sheets A–C of FIG. 2.

FIG. 4 shows another design having aligned channels 106, 108. Inlets, outlets and fluid passages are the same as in FIG. 2. In the assembled device, the channel formed by 106, 108 contains the adjacent first and second phase streams.

Figure 5:
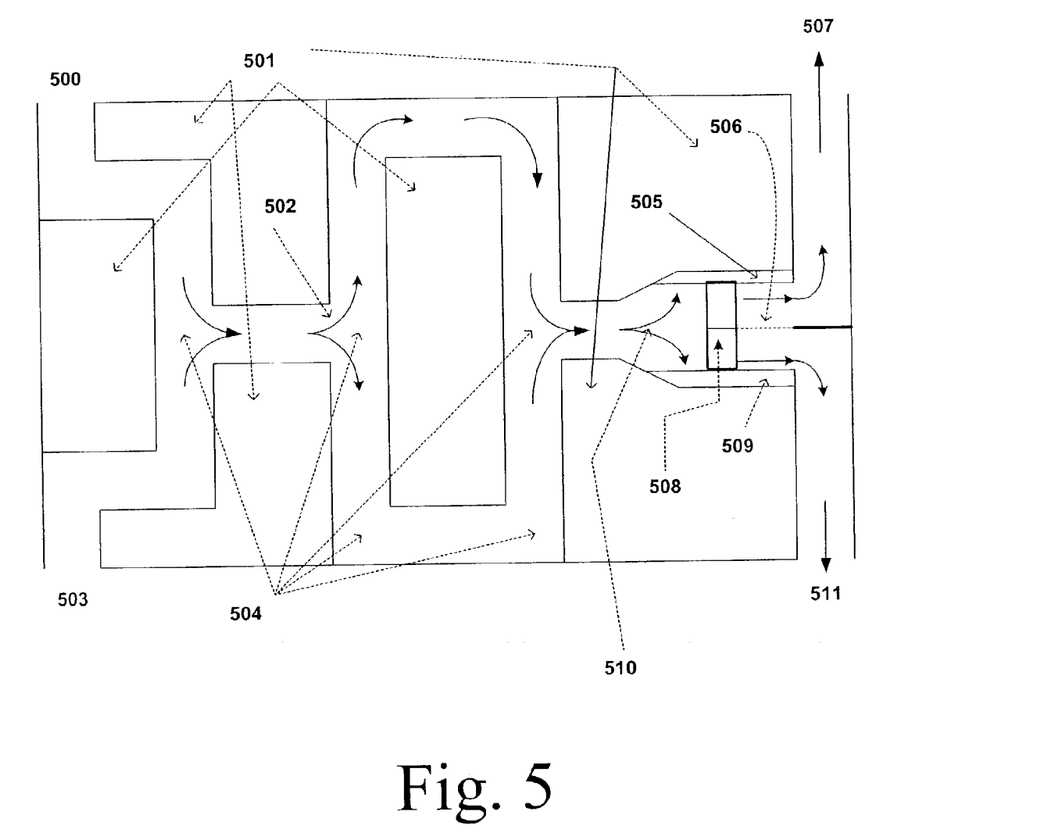
FIG. 5 is a schematic, cross-sectional view of a microreactor for phase transfer catalysis. Fluid flows are also shown.

Another inventive embodiment is illustrated in FIG. 5. In this embodiment, flows of immiscible streams pass through inlets 500 and 503. The streams meet at a point 502 where, in some cases, the streams combine to form an emulsion. In a typical phase transfer reaction, one or both of the streams contain a PTC. The combined stream 504 flows through microchannels having a series of sharp (80 to 100°, more preferably 85 to 95°) turns that can help maintain a fine dispersion.

The stream then flows into separation zone 510. The separation zone contains at least one wall (or wall portion)

509 that is hydrophilic and at least one wall (or wall portion) 505 that is hydrophobic. Hydrophilic and hydrophobic surfaces are well-known and include coatings such as hydrophilic silica or plasma-treated polymer and hydrophobic polymer coatings such as tetrafluoropolyethylene; alternatively such surfaces could be an inherent characteristic of the materials selected to construct the device. In the present invention, the separator zone should have at least one dimension that is less than 2 mm in order to reduce separation (and mass diffusion) times; preferably, the separation between hydrophilic and hydrophobic surfaces is less than 2 mm, more preferably less than 1 mm.

In some preferred embodiments, the opening to the separation zone gradually widens 510 to slow the flow. Optionally, the separation zone may contain a coalescence element 508, that could be, for example, fibers, foam, or slats. Preferably, the separator zone contains a separator plate 515 that preferably has a hydrophilic side and a hydrophobic side to assist in the phase separation (in this case the hydrophilic side is on the side of aqueous phase that is directed to outlet 511). The separator plate may be solid or porous. Preferably, there is a porous plate or screen 506 that allows some fluid exchange between the partly separated streams. The plate or screen 506 may also have hydrophilic and hydrophobic sides (in either orientation—corresponding to the hydrophilicity of the streams or opposite thereto). In one preferred embodiment, the article is constructed by forming (such as by etching) flow paths around lands 501 in a plate; in another alternative, designs could be stamped in sheets, and the sheets stacked and bonded to make the illustrated reactor.

Figure 6A:
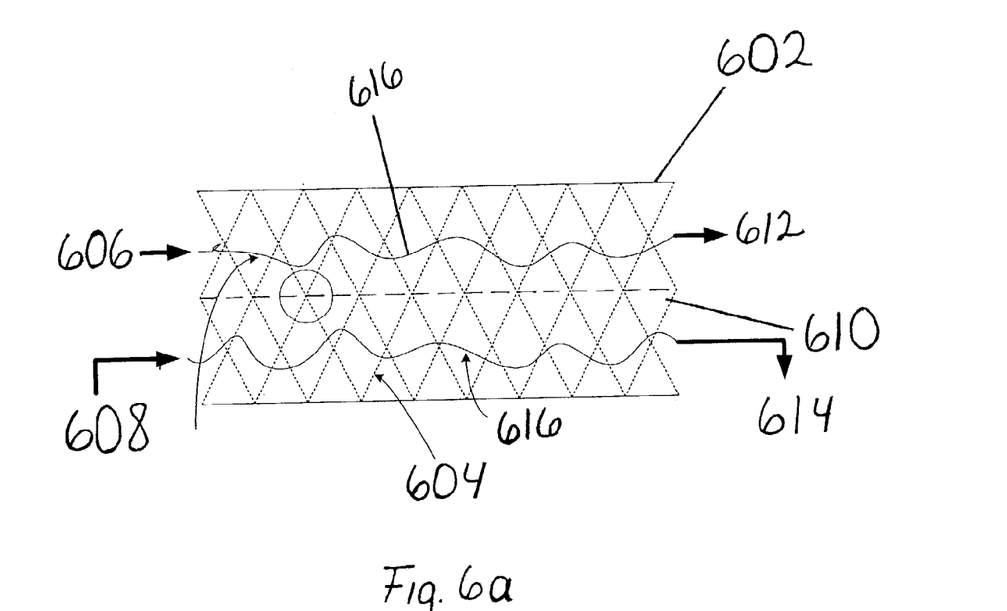
FIG. 6a schematically illustrates a triphasic system with a porous ionic exchange material.
Figure 6B:
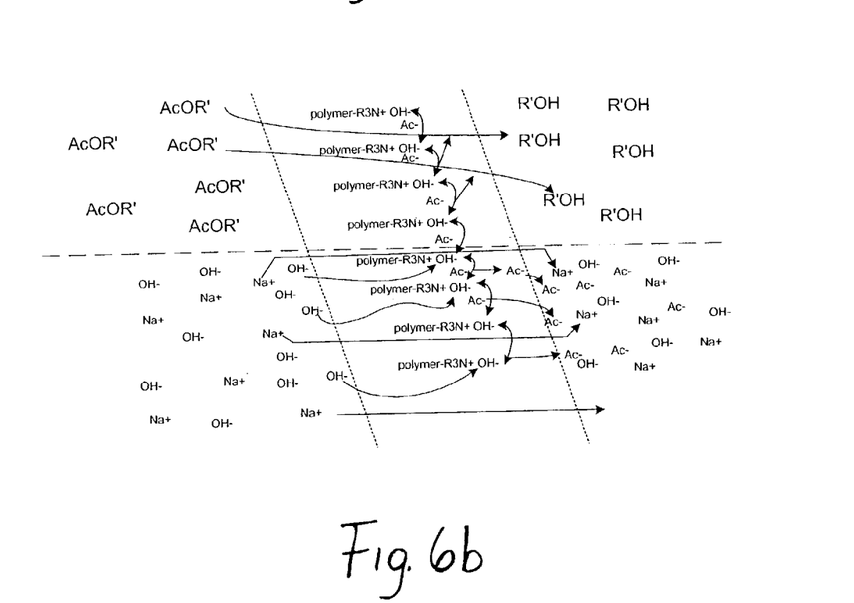

FIGS. 6a and 6b shows a cross-sectional view of a microchannel 602 (preferably having a height (the dimension perpendicular to flow and in the plane of the page) of 1 micrometer or less) that is filled with a porous ionic membrane (a solid PTC) 604 as beads, screen, slats, film, etc. A water immiscible phase 606 containing a non-water soluble reactant contacts an aqueous phase 608 containing a water soluble reactant at interface 610. A reaction takes place through the PTC (for example, hydrolysis of H3CC(O)OR shown in FIG. 6b) to produce product streams 612, 614.

Preferred microchannel reactors are characterized by the presence of at least one reaction channel having a (wall-to-wall, not counting catalyst) dimension of 2.0 mm (preferably 1.0 mm) or less, and in some embodiments 50 to 500 µm. Both height and width are perpendicular to the direction of flow. The height and/or width of the reaction microchannel is preferably about 2 mm or less, and more preferably 1 mm or less (in which case the reaction chamber falls within the classical definition of a microchannel). The length of the reaction channel is typically longer. Preferably, the length of the reaction chamber is greater than 1 cm, in some embodiments in the range of 1 to 20 cm. Typically, the sides of the reaction channel are defined by reaction channel walls. These walls can be made of any desired material such as ceramic, iron based alloys such as steel, nickel, titanium, or other metal alloy, or silicon. In some preferred embodiments, the walls of the reaction channels are a plastic material which can have good solvent resistance and can be relatively inexpensive, with unfilled, or perferably, filled, thermosets and thermoplastics being acceptable. Filled plastics are often most preferred since their limited tendency to shrink allows them to be used as engineered resins since they can be fabricated to tight tolerances. In some preferred embodiments, the microchannel walls are treated or coated to obtain the desired degree of hydrophobicity or hydrophilicity, as defined previously. The degree of hydrophobicity and hydrophilicity can be quantified using contact angle. The reactors can be made by known methods, and in some preferred embodiments are made by laminating shims cut or stamped from flat stock material, or molded.

The reactors preferably include a plurality of microchannel reaction channels to maximize the full benefits of the microprocessing technology ("MPT") design. The device would normally also contain, in those cases where temperature control is needed, and/or a plurality of adjacent heat exchanger microchannels. The plurality of microchannel reaction channels may contain, for example, 2, 10, 100, 1000 or more channels within a planar layer and 2, 10 100 or more stacked layers, preferably stacked, with alternating heat exchange layers (preferably microchannel heat exchangers) if temperature control is desired due to the nature of the reaction chemistry, i.e. whether the reaction is significantly exothermic or endothermic. In preferred embodiments, the microchannels are arranged in parallel arrays of planar microchannels. Microchannel reactors and their construction methods (especially sheet-type construction) are known and these reacotr designs and manufacturing techniques can be adapted and modified to construct microchannel reactors for phase transfer reactions. Performance advantages in the use of this type of reactor architecture for the purposes of the present invention include their ability to form flow streams with a very large surface area to volume ratio and their ability to form laminar flow streams. Furthermore, use of microchannel reactors can achieve better temperature control, and maintain a relatively more isothermal profile, and precisely controlled distribution of residence times compared to architectures of the prior art. This, in turn, advantageously leads to lessened peak temperatures and lessened side reactions.

Preferably, the reaction microchannel (or microchannels) contains a bulk flow path. The term "bulk flow path" refers to an open path (contiguous bulk flow region) within the reaction chamber. A contiguous bulk flow region allows rapid flow through the reaction chamber without large pressure drops. In preferred embodiments there is laminar flow in the bulk flow region. Bulk flow regions within each reaction channel preferably have a contiguous cross-sectional area of $5\times10^{-8}$ to $1\times10^{-2}$ m$^2$, more preferably $5\times10^{-7}$ to $1\times10^{-4}$ m$^2$. A preferred relationship between cross section area, liquid flow velocity, and laminar regime to define operational range was given above in the Reynold's number equation. The bulk flow regions preferably comprise at least 5%, more preferably 30–100% of either 1) the internal volume of the reaction chamber, or 2) the cross-section of the reaction channel.

In addition to the reaction microchannel(s), additional features such as microchannel or non-microchannel heat exchangers may be present. If present, the heat exchanger is preferably an integrated (for example, interleaved) heat exchanger. The heat exchange fluids can be gases or liquids and may include steam, liquid metals, water, Therminol®, mineral oil, silicone oil, brine, or any other known heat exchange fluids—the system can be optimized to have a phase change in the heat exchanger. In some preferred embodiments, multiple heat exchange layers are interleaved with multiple reaction microchannels (for example, at least 10 reaction microchannels interleaved between at least 10 heat exchangers).

In some embodiments (for nonlaminar flow or to generate a first emulsion stream that is subsequently reacted with a second immiscible stream in a laminar fashion), two immiscible flow streams can be passed through a microchannel mixer that is separate or integral with the reaction microchannel. In this case, two fluids can be pumped through a channel which is divided by a blade or shim orthogonal to the walls (and often also spiraled). The blade is short and so the divided fluids can be sent against a second, then third, etc. sequence of blades. This means of subdividing the two phases generates small emulsion droplets yet usually not the semi-stable emulsion that would form in a normal mixer using an impeller. Ten to fifteen such blades usually suffices for an excellent droplet-sized emulsion.

Another optional element is a wick selected for the interaction with a phase to form a layer—this wick could be inserted or formed on one side of a channel. Wicks can be microchannels on a wall, etc. In other embodiments, no wick is present in the channel. In the illustrated embodiments, flow of one phase enters through one side of a channel and out at the opposite side; however, in alternate structures, feed can be delivered or removed at multiple points along the length of a channel. Rectangular channels are illustrated, however other shapes can be employed.

The inventive methods utilize a PTC. In some embodiments, a channel can also contain additional catalysts. The additional catalyst, if present, can be, for example, a porous catalyst material or more preferably a coating on a part of the interior of a channel, such as a washcoat on one side of a four-sided channel. The catalyst can comprise a support and an overlying layer or layers of active catalyst sites and an optional intervening layer or support material (which could be used to increase adhesion and/or surface area; a metal oxide is one type of intervening layer (by "intervening layer" it is not meant that the intervening layer is necessarily distinct from the active sites, in many cases the active sites will be dispersed in crevices or holes in the intervening layer. In some preferred embodiments, the catalyst(s) layer is selected to attract or repel a phase (for example, a hydrophilic or hydrophobic catalyst layer).

Catalytically-active material that may be present in addition to the PTC is not particularly limited and may include any effective prior art catalyst. Among the catalytically-active materials usable in the present invention include noble metals, preferably catalyst materials comprising at least one metal selected from the group consisting of Pt, Pd, Rh, Ir and Ru. Other catalytically-active materials include at least one oxide or phosphate of a metal selected from the group consisting of Li, Mo, V, Nb, Sb, Sn, Zr, Cr, Mg, Mn, Ni, Co, Ce, rare-earth metals and mixtures thereof. The catalyst may contain additional components such as alkalai or alkaline earth promoters. Preferred catalyst support materials include alumina, silica, other metal oxides, mesoporous materials and refractory materials. Catalysts can also be a noble metal dispersed on a metal oxide layer that is coated over (such as by wash coating or chemical vapor deposition) a metal foam or metal felt (nonwoven metal). In some preferred embodiments, catalyst is disposed (such as by CVD or wash coating) on a wall or walls (or only a portion of a wall) of a microchannel. Where the catalyst is exposed on an interior channel surface, the interaction with a phase stream should be considered. Especially preferred catalysts include tethered catalysts in which an ordinarily soluble catalyst is anchored to a microchannel wall by a covalent attachment. Preferred catalysts will not cause mixing within a reaction microchannel.

Methods

Methods of the invention use at least two distinct phase streams that are in direct contact (with no intervening membrane). In preferred embodiments, the methods are conducted in the apparatus described herein. Typically, the method will involve one aqueous phase and one immiscible organic phase; however, in some embodiments other combinations can be used. In some less preferred embodiments, more than 2 phases could be present in a microchannel, for example, the aqueous phase could itself be an emulsion and contain a dispersed third phase.

The methods can also include additional processing steps such as recycling solvent, catalyst and/or reactant back into an inlet for additional use. For example, in a step subsequent to reaction, product can be removed by a separation technique such as distillation, precipitation or membrane filtration, and the solvent, catalyst and/or reactant recycled.

In general, the inventive methods can be applied with good effect to any known phase transfer catalyzed reactions. Two examples of conventional phase transfer catalysis are described in U.S. Pat. Nos. 5,347,043 and 5,514,189 which are incorporated herein by reference Particular phase transfer catalyzed reactions believed to be especially well-suited for use in the present invention include: alkylations, dehydrohalogenation, esterification, hydrolysis, oxidation, epoxidation, Michael addition, Aldol condensation, reductions, and carbonylation. Some of the specific preferred conditions, temperatures, pressures, solvents, flow regimes, etc. are given in the Examples Section. For example, the inventive methods can be used to condense alcohols to form ethers in the presence of a PTC such as a quaternary ammonium ion. Similarly, esterification reactions can be conducted in the presence of a quaternary ammonium ion or crown ether PTC.

The following is a nonlimiting list of the types of reactions that can be carried out by phase transfer catalysis of the present invention: SN2 displacement reactions with alkyl halides and anions: $CN^-$, $SCN^-$, $CNO^-$, $F^-$, $Cl^-$, $Br^-$, $I^-$, $N_3^-$, $SH^-$, $HSO_3^-$, $RS^-$, $ArO^-$, $RCO_2^-$, etc.; alkylation reactions using NaOH (aq) and alkyl halides: for C-alkylations—activated nitriles, ketones, esters, nitro-compounds, cyclopentadienes, and other acidic C–H compounds, for N-alkylations—imides, amides, sulfoamides, and heterocyclic N-compounds, and S-Alkylations; other Strong Base Reactions such as: O-Alkylations (etherification), dehydrohalogenation, carbene reactions, condensation reactions, Micheal Addition, Aldol Condensation, Wittig, Darzens; synthesis of alpha-hydroxy acids; elimination reactions to produce olefins and acetylenes, oxidation reactions of many compounds using inorganic oxidants such as $MNO_4^-$, $OCl^-$, $H_2O_2$, $O_2$, $IO_4^-$, $HNO_3$, etc.; reduction reactions of many compounds with: $BH_4^-$, $AlH_4^-$, $HCO_2^-$, etc., polymerization reactions and polymer modifications; and reactions containing transitional metals as cocatalyst such as carbonylation, carboxylation, and hydrogenation.

Factors affecting the reactivity of a PTC system include agitation (if present), catalyst, anion type, solvent, reactive constituent concentrations, and temperature. These factors affect the rate of transfer of the reactive constituent into the organic phase and the intrinsic reaction rate within the organic phase. With these factors in mind, microchannel devices are able to provide PTC reaction benefits over tradition PTC reactor technologies by providing a controlled micro-environment that maximizes the production of the target compound.

An optimized micro-environment would have a very large surface area for interphase transport, the correct ratio of reactants and catalyst, good mixing, and appropriate temperature control. Currently, most PTC reactions are done in mixed reactor vessels. Control of particle size (surface area) and mixing are accomplished through turbine or other type of agitation. Temperature control is provided by heat exchange through reactor walls or internal/external heat exchanger.

For some non-laminar flow embodiments of the present invention, an oil-in-water microemulsion can be generated in a microchannel reactor. The particle size of this emulsion can be smaller than that produced by traditional batch techniques. The particle size should be maximized to produce transfer rates that will allow the reaction to be completed within a short residence time within a microchannel system, but not so small as to require excessive separation time of the phases. This microemulsion concept applies to PTC soluble liquid-liquid systems and PTC insoluble organic-PTC-aqueous systems.

For faster or more complete reaction, the temperature of the system should be maximized. Higher temperatures promote improved transfer rates and intrinsic reaction rates. Sensitivity must be given to the temperature stability of the phase transfer catalyst. Because of the significant improvement in the heat transfer surface area to reactor volume provided by microchannel technology, higher reactor temperatures should be able to be safely run without affecting the integrity of the catalyst and the final product.

Some reactions that conventionally suffer from slow anion exchange rates and slow intrinsic reaction rates can be improved by the inventive methods. The classic example of a reaction in this type of reaction is the fluoride displacement reaction on 2-chloroalkanes. The transfer of fluoride into the organic phase is difficult because it has a high charge to volume ratio and is the most strongly hydrated ion. Once transferred into the organic phase by the phase transfer catalyst, the flouride ion is a poor nucleophile, so displacement reaction rates are low. There are chemistry approaches that improve the rate of transfer of constituents between the aqueous and organic phase such as using two different phase transfer catalysts. To improve the overall rate of reaction, increased mixing rate (increased transfer rate/surface area) and higher reaction temperatures are also recommended. A microchannel PTC device could provide a significant improvements in reaction rates by providing an microenvironment of high diffusional surface area, and good temperature control. As noted earlier, a microchannel device should be able to run at higher reaction temperatures than conventional methods since good heat transfer would lower the overall temperature differential between the heat transfer surface and the reaction fluid.

Some PTC reactions have fast anion transfer rates and fast intrinsic kinetics. A representative reaction is permanganate oxidation of olefins. The permanganate ion is easily transferred into the organic phase via the PTC. The permaganate ion then reacts vigirously with oxidizable groups in the organic phase. The main concern with this type of system is reaction control. The heat transfer advantage of a microchannel PTC reactor should allows for improved reaction rate control and product selectivity.

PTC reactions that are rate limited by anion transfer rate are represented by reactions such as C-alkylation of phenylacetonitrile (e.g. ethylation, butylation). For these reactions, the aqueous phase may be a concentrated NaOH solution. The transfer rate of the hydroxide ion or its reactive intermediate is slow, so this reaction conventionally benefits from increased agitation rates to improve interfacial transfer rates and increase overall transfer surface area. For this reaction, literature shows a fairly linear coorelation between agitation rate and overall reaction rate. Because of the transfer rate issues, the C-alkylation reactions times can be high to provide high yield levels, >30 minutes. This is also true with other PTC reactions using aqueous NaOH: N-alkylations and O-alkylations. The greater relative interfacial transfer rates provided by the inventive PTC microchannel reactors can result in signicantly higher overall reaction rates and decreases in overall cycle time.

An example of a PTC reaction where the intrinsic rate of reaction in the organic phase controls the overall reaction rate is the cyanation of alkylbromide. Studies have shown that the reaction rate for this reaction in conventional PTC systems increases steadily with agitation to a point and then no additional benefit is observed. In this case, leveraging the enhanced heat transport capabilities of a microchannel device could provide yield benefits by allowing the reaction to run at higher temperatures (with controlled residence time) to increase intrinsic reaction rates.

EXAMPLES

All of the following examples are prophetic examples—the examples describe various advantages provided by the inventive PTC methods; however, the examples do not report the results of actual experiments conducted in microchannel apparatus.

Example 1

Conventionally, cyclohexane oxidation is cautiously oxidized with air in large vats in manufacturing cyclohexanone-cyclohexanol ketone-alcohol blend (K-A), the intermediate in manufacturing commodity chemicals such as adipic acid food acidulant and nylon 6,6 intermediate. Only about 4% conversion of the hexane to K-A is allowed to occur per pass to avoid igniting the hot hexane/air mixture caused by present of peroxide and other intermediates. The per pass conversion is also limited for economic reasons, as over oxidation produces wasteful by-products of dicarboxylic acids of shorter chain length (C4, C5), which can only be purged from the process and product by wasting significant quantities of the product, adipic acid. In addition it is very difficult to contact the catalyst, for example cobalt or boric acid, with the hexane due to low solubility in this solvent, requiring intense mixing operations. Also, the highly exothermic reaction could readily cause the system to overheat causing dangerous boiling in the large vats, with product decompositin, or reaction "run away" (i.e. large amounts of unwanted by-product production). The low percent conversion per pass results in having to purify and recycle large amounts of hexane and catalyst, in fact about 96% of the mass in the operation is in the recycle loop, not in the product line. Substantial over-reaction still occurs as more than 50 by-products are produced and have to be disposed of. The presence of toxic elements (Co or B) from the catalyst make it environmentally unacceptable to burn this waste as fuel, or to send it to biotreatment of waste. Hence there are many reasons why a better alkane air oxidation process is needed.

Biphasic microtechnology processing "MTP" is projected to significantly improve the K-A production process by safely providing much higher conversions per-pass, with much higher selectivities (less by-product production), and less waste production. Note that even 0.5% per pass conversion increase is significant as this represents a 12.5% production rate increase. Per pass yields expected from biphasic MTP of much larger amounts are expected and represent the preferred case. For example 8–16% conversion per pass, or 100–400% production rate increases, are possible due to the biphasic MTP technology for the following reasons, 1) The small chemical content inventory in the MTP reactor at any instant allows reaction conditions to be used that would be hazardous in conventional apparatus, for example higher temperature and/or higher air content (mole O2/mole hexane), since any reaction excess vigor would behave harmlessly, and could easily be regulated by controlling the entry rate of one or more of the raw material feed rates, for example the air injection rate, and the response would be within seconds, rather than hours.

2) By efficient heat removal afforded by the very high internal surface area/volume ratio of the MTP reactor with a heat exchanger surface built into the MTP reactor. The faster the heat removal, the faster the production rate of K-A and the lower the by-product formation.

3) By allowing intimate mixing with the MTP reactor between the three phases: air, catalyst and hexane (see Figure) the process parameters can be adjusted to produce higher K-A product yields while maintaining, and preferrably decreasing, by-product formation rates and quantities.

4) By allowing more efficient, but more expensive PTC to be used due to the small working volume of the MTP hardware. This is an important advantage over conventional processing. For example, when the catalyst is the preferred boric acid, the PTC could be selected to be a di- or poly-alcohol selected specifically to maximize solubility of boric acid in very non polar solvents, i.e. hexane in this case. Notice that the actual concentration of PTC and catalyst in the hexane will preferrably increase over conventional practice providing the enhancements described.

5) Since a performance PTC is being used due to the small working capital level of MTP, very cheap inorganic bases can be used for the neutralization, for example sodium carbonate, potassium hydroxe, etc. The PTC would contact these materials in an external loop then circulate back into the MTP device at a high recycle rate.

6) The increase in efficiency and safety may also make the use of pure oxygen viable, which then increases productivity still further since the substantial amount of nitrogen gas handled is then reduced, allowing more space for reacting chemicals.

Example 2

Most aldehydes are difficult compounds to make due to the ease at which the reaction proceeds too far. For example, in making an aldehyde, RCHO, by oxidizing an alcohol, ROH, major loss in yields occur due to the overoxidation to the carboxylic acid, RCOOH, i.e.,

| | |
|---|---|
| ROH + oxidant → RCHO | (desired reaction) |
| RCHO + oxidant → RCOOH | (unwanted over-reaction) |

Suitable oxidants are hot, acidic potassium dichromate, chlorochromate, permanganate, etc. with a PTC that is oxidation resistant such as pyridinium ion, $C_5NH_5^+$, (py$^+$) and its derrivatives. For example pyridinium chlorochromate (*Merck Index*, Vol. 12, number 8157, page 8153). Another example is potassium permanganate oxidant with 18-crown-6 as the PTC. For example, n-propanol is oxidized to propylaldehyde, $CH_3CH_2CHO$ in only 45–49% yield using potassium dichromate acidified with sulfuric acid at boiling conditions (*Organic Synthesis* Coll. Vol. 2, 541). MTP with either of the above mentioned PTC would be expected to provide substantially better yields and purer product than this.

On the other hand, should the carboxylic acid be wanted, then the permanganate oxidant is preferred over the chromate, but with the same or similar PTC. The two phase system allows very water insoluble product carboxylic acids to be produced if PTC are employed. For example $CH_3(CH_2)nOH$ alcolols, whre n=12, 15 or 21, are oxidized to the carboxylic acid in yields of 92, 95 and 87% (p 219 of Manganese Compounds as Oxidizing Agents in Organic Chemistry by Diether Arndt (Open Court Publ. Co., LaSalle, Ill., (1981), which are good yields but, given the nature of large scale commodities, as these fatty acids are, even a ½% yield enhancement is attractive. Hence the combined MTP and PTC technology of the invention can be expected to enhance these yields by at least several percent or more.

Example 3

Mono substituted hydroxylamines, RNHOH, are difficult compounds to make due to the ease at which the reaction proceeds too far. For example, in making RNHOH by reducing a nitroalkane liquid, $RNO_2$, by heating with a Pd-based catalyst in hydrogen gas major loss in yields occur due to the over-reduction to the amine, RNH2 i.e.,

| | |
|---|---|
| $RNO_2 + H_2 \rightarrow RNHOH$ | (desired reaction) |
| $RNHOH + H_2 \rightarrow RNH2$ | (unwanted over-reaction) |

For example R can be Me-, Et-, nPr-, iPr, nBu-, iBu-, $C_6H_5$—, $MeC_6H_5$—, xylenes, naphthalenes, 2-ethylhexyl-, etc.

PTC MTP technology is an excellent solution to this problem for the following reasons: 1) only small amounts of the heated nitroalkane, an explosive blend, be contained in the reactor at any one time. 2) the intimate mixing (Figure) of the two (aqueous base and nitro-alkane liquid), allows the PTC, a quaternary ammonium hydroxide, to bring the reactants togehter in intimate contact and uniformly. Hence reactant concentrations will vary less, allowing higher process production yields.

Example 4

Carbonization or polymerization of delicate and/or reactive olefins can occur by over-thermolysis while reacting other parts of a molecule. In this case the MTP-PTC technology provides the very short resisdence time required to avoid or minimize unwanted side reactions. For example the hydrolysis of methyl acrylate to acrylic acid using quarternary ammonium hydroxide or acid PTC, i.e.,

RCOOR'+PTC+base/acid (source of OH$^-$/H$^+$ for the PTC)→RCOOH/Na+R'OH

Note that the base/acid source, and aqueous solution or a solid for PTC systems can be external to the MTP reactor. Such an arrangement allows very low cost bases (e.g. soda ash, lime, sodium hydroxide, potassium carbonate, potassium hydroxide, etc.), and acids (strong acid resins, petroleum sulfonic acid, sulfuric acid, hydrochloric acid, etc.), to be used. In such a case, the PTC is circulated many times through the external acid/base to minimize the quantity of PTC needed per unit weight of hydrolyzed product produced.

Example 5

The chemical and pharmaceutical indsutry use cyano hydrins as intermediates for a range of compounds. The reaction involves highly reactive and poisonous compounds—aldehydes and hydrogen cyanide. The base catalyzed reaction is

RCHO+HCN→RCH(OH)CN

In this case, the MTP-PTC technology of the invention minimizes the risk posed from large quantities of hazardous (carcinogenic and poisonous) materials. Instead of large reaction vats the HCN is generated only in small (but continuous) quantities immediately prior to use. This point-of-use MTP process involves the flowing together of an aqueous stream of sodium cyanide, (the low-cost and safely handled form of cyanide ion), and sulfuric acid, i.e., H$_2$SO$_4$(aq)+NaCN(aq)→HCN+NaHSO$_4$+heat The heat of this and the synthesis reaction is removed by the MTP heat exchanging feature, thereby preventing decomposition of the reactive cyano hydrin and unwanted hydrolysis of the HCN intermediate or cyano hydrin product.

Optionally, within the same MTP device, the HCN is brought together to react with a stream of aldehyde. The PTC can be added with, before or after the two streams come together. As the product is very water soluble, it is beneficial to add the PTC along with the aldehyde in the nonaqueous phase.

When the carbon number of the R group renders the aldehyde of low aqueous solubility (e.g. C#>5) then a PTC is added to speed the reaction by transporting hydroxide ion (or any ther suitable base) into the nonaqueous phase containing the alkdehyde. A preferred PTC in this case is tetraalkylammonium hydroxide.

Notice that this cyanohydrin chemstry can be used with very sensitive molecules, even sugars, to extend the carbon number by one or to make nitriles. Hence, MTP-PTC will minimize decompostion of products and raw materials, and increase product yields.

Example 7

As a more specific example of cyano hydrin production, acetone is converted to a cyano hydrin, i.e., (Ref: *Organic Synthesis*, Collective Volumes 2, 7).

Hence MTP with PTC would produce this cyano hydrin at at least 77% yield, preferrably >90%, and with less impurities, and much faster due to efficient heat removal.

Example 8

Aldol Condensation reactions are very important organic synthesis chemical reactions and have been for many years for both the lab to industrial scale. The reaction couples two aldehydes to form an "aldol", i.e. a β-hydroxy aldehyde. Alpha hydrogens are important for the reaction to occur, i.e.

This reaction is base catalyzed. Hence, PTC is effective in promoting this reaction when the aldehyde is not very water soluble. Especially preferred as the PTC are the tetraalkylammonium hydroxides. Undesirably, when two different aldehydes are blended, or aldehyde plus ketone combinations are made, all possible condensation products are found. This result greatly lowers the yield and complicates separations.

By carrying this reaction out in the MTP+PTC combination, advantanges are expected in selectivity and yield. These benefits would arise by the ability of MTP to control reaction conditions closely, including residence time, base activity and reactivity, mixing conditions, order of addition, temperature profiles, etc.

While preferred embodiments of the present invention have been described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method of conducting a chemical reaction, comprising:
   passing a first stream and second stream into a reactor channel;
   wherein the first stream has a thickness of 1 mm or less and a length of more than 3 mm through the reaction channel;
   and wherein the second stream is adjacent to the first stream and has a thickness of 1 mm or less and a length of more than 3 mm through the reaction channel;
   wherein the first stream and the second stream form a combined multiphase stream having a thickness of 2 mm or less and a length of more than 3 mm;
   wherein the first stream comprises a first reactant;
   wherein the second stream comprises a second reactant; and
   providing a phase transfer catalyst;
   wherein the phase transfer catalyst catalyzes the reaction of the first reactant and the second reactant to form a product.

2. The method of claim 1 wherein the method is conducted in a reactor that comprises a first stream inlet, a reaction channel comprising a reaction zone, a first stream outlet disposed such that the first stream enters through the first stream inlet, travels through the reaction channel and out through the first stream outlet and wherein the first stream is continuous over the entire length of the reaction channel; and
a second stream inlet, a reaction channel comprising a reaction zone, a second stream outlet disposed such that the second stream enters through the second stream inlet, travels through the reaction channel and out through the second stream outlet and wherein the second stream is continuous over the entire length of the reaction channel.

3. The method of claim 2 wherein the first stream is aqueous and the second stream is organic and the phase transfer catalyst is soluble in at least of the first and second streams.

4. The method of claim 1 wherein the first stream is aqueous and the second stream is organic.

5. The method of claim 4 further comprising a step of separating a product from the second stream.

6. The method of claim 4 further comprising a step, subsequent to the reaction step, of separating a PTC from at least one of the streams; wherein the step of separating comprises separating the PTC from a solvent, a product, or both a solvent and a product.

7. The method of claim 6 further comprising a step of recycling the separated PTC back into a reaction channel.

8. The method of claim 4 wherein the method comprises a reaction selected from the consisting of alkylations, dehydrohalogenation, esterification, hydrolysis, oxidation, epoxidation, Michael addition, Aldol condensation, reductions, and carbonylation.

9. The method of claim 4 wherein the PTC is selected from the group consisting of: a quaternary ammonium compound, a quaternary arsonium compound, a quaternary phosphonium compound, a crown ether, and an organocobalt compound.

10. The method of claim 9 further comprising a cocatalyst.

11. The method of claim 4 wherein the PTC is a porous solid.

12. The method of claim 4 further comprising exchanging heat of reaction; wherein heat is added to the reaction channel from a fluid in an adjacent heat exchanger through a reaction channel wall or wherein heat is removed from the reaction channel to a fluid in an adjacent heat exchanger through a reaction channel wall.

13. The method of claim 4 further comprising exchanging heat of reaction; wherein heat is added to the reaction channel through a reaction channel wall or wherein heat is removed from the reaction channel through a reaction channel wall.

14. The method of claim 4 wherein the phase transfer catalyst is soluble in both the first stream and the second stream.

15. The method of claim 4 wherein the phase transfer catalyst is insoluble in both the first stream and the second stream.

16. The method of claim 4 wherein the aqueous first stream comprises an emulsion.

17. The method of claim 1 wherein the first stream has a thickness of 100 µm or less.

18. A method of conducting phase transfer catalysis, comprising:
  passing a first stream and a second stream into a reactor channel;
  wherein the reactor channel has a thickness of 2 mm or less and a length of more than 3 mm;
  wherein the first stream comprises a first reactant;
  wherein the second stream comprises a second reactant; and
  providing a phase transfer catalyst;
  wherein the phase transfer catalyst catalyzes the reaction of the first reactant and the second reactant to form a product.

* * * * *